(12) United States Patent
Haye et al.

(10) Patent No.: US 11,536,706 B2
(45) Date of Patent: Dec. 27, 2022

(54) ACTIVE OIL DEBRIS MONITOR PHASE ANGLE CALCULATION AND MONITORING SYSTEM

(71) Applicant: United Technologies Corporation, Farmington, CT (US)

(72) Inventors: Sheridon Everette Haye, Mansfield, CT (US); Edward Thomas Rocco, Rocky Hill, CT (US)

(73) Assignee: Raytheon Technologies Corporation, Farmington, CT (US)

( * ) Notice: Subject to any disclaimer, the term of this patent is extended or adjusted under 35 U.S.C. 154(b) by 919 days.

(21) Appl. No.: 16/278,410

(22) Filed: Feb. 18, 2019

(65) Prior Publication Data

US 2020/0264158 A1   Aug. 20, 2020

(51) Int. Cl.
*G01N 33/28*   (2006.01)
*F01D 25/18*   (2006.01)

(52) U.S. Cl.
CPC ......... *G01N 33/2888* (2013.01); *F01D 25/18* (2013.01); *G01N 33/2823* (2013.01); *G01N 33/2858* (2013.01); *F05D 2220/32* (2013.01); *F05D 2260/40311* (2013.01); *F05D 2260/83* (2013.01); *F05D 2260/98* (2013.01)

(58) Field of Classification Search
CPC ........... G01N 33/2888; G01N 33/2823; G01N 33/2858; F01D 25/18
See application file for complete search history.

(56) References Cited

U.S. PATENT DOCUMENTS

| | | | |
|---|---|---|---|
| 5,001,424 A | 3/1991 | Kellett et al. | |
| 5,061,070 A | 10/1991 | Batchelder et al. | |
| 5,315,243 A | 5/1994 | Kempster et al. | |
| 5,444,367 A * | 8/1995 | Kempster | G01V 3/107 324/225 |
| 6,051,970 A | 4/2000 | Hutchings | |
| 6,348,087 B1 | 2/2002 | Aslin | |
| 6,377,052 B1 | 4/2002 | McGinnis et al. | |
| 6,459,995 B1 | 10/2002 | Collister | |
| 6,839,620 B1 | 1/2005 | Koehler et al. | |
| 6,850,865 B2 | 2/2005 | Hirthe et al. | |
| 6,984,986 B2 | 1/2006 | Sosnowski et al. | |

(Continued)

FOREIGN PATENT DOCUMENTS

| | | |
|---|---|---|
| CN | 103217366 A | 7/2013 |
| EP | 2964929 A1 | 1/2016 |
| WO | 2014138432 A1 | 9/2014 |

OTHER PUBLICATIONS

EP Search Report dated Aug. 25, 2020 issued for corresponding European Patent Application No. 20158076.8.

(Continued)

*Primary Examiner* — Bryan Bui
(74) *Attorney, Agent, or Firm* — Bachman & LaPointe, P.C.

(57) ABSTRACT

A method for actively calculating and monitoring the oil debris monitor phase angle includes sensing a noise from an in-line oil debris monitor sensor in an oil flow path, generating a polar plot of an I and Q channel data from only the noise. Linear regression of noise is then utilized from the I and Q channel data for calculating a slope of regression form the linear regression and converting the slope to a phase angle.

19 Claims, 11 Drawing Sheets

(56) References Cited

U.S. PATENT DOCUMENTS

| | | | |
|---|---|---|---|
| 6,989,680 B2 | 1/2006 | Sosnowski et al. | |
| 7,043,402 B2 | 5/2006 | Phillips et al. | |
| 7,288,138 B2 | 10/2007 | Showalter et al. | |
| 7,457,603 B2 * | 11/2008 | Smith | H01Q 3/26 |
| | | | 455/226.1 |
| 7,581,434 B1 | 9/2009 | Discenzo et al. | |
| 7,956,601 B2 | 6/2011 | Becker et al. | |
| 7,983,864 B2 | 7/2011 | Hu et al. | |
| 8,340,928 B2 | 12/2012 | Sun | |
| 8,826,741 B2 | 9/2014 | Kuehl et al. | |
| 9,354,094 B2 | 5/2016 | Sinha | |
| 10,302,541 B2 * | 5/2019 | Hagen | F01D 21/10 |
| 2006/0079192 A1 | 4/2006 | Smith | |
| 2008/0054914 A1 | 3/2008 | Byington et al. | |
| 2009/0051350 A1 | 2/2009 | Becker et al. | |
| 2010/0109686 A1 | 5/2010 | Zhe et al. | |
| 2010/0126251 A1 | 5/2010 | Pileggi et al. | |
| 2011/0224917 A1 | 9/2011 | Uluyol et al. | |
| 2012/0055264 A1 | 3/2012 | Sinha | |
| 2015/0343346 A1 | 12/2015 | Sheridan | |
| 2016/0017747 A1 | 1/2016 | Pamin et al. | |
| 2017/0138217 A1 | 5/2017 | Schwarz et al. | |
| 2017/0350842 A1 | 12/2017 | Mohr et al. | |
| 2018/0023414 A1 | 1/2018 | Hagen et al. | |
| 2018/0135455 A1 | 5/2018 | Khibnik et al. | |
| 2018/0231497 A1 | 8/2018 | Glaberson et al. | |
| 2018/0266938 A1 | 9/2018 | Chow | |
| 2020/0264135 A1 | 8/2020 | Rocco et al. | |
| 2020/0264157 A1 | 8/2020 | Rocco et al. | |

OTHER PUBLICATIONS

EP Search Report dated Sep. 8, 2020 issued for corresponding European Patent Application No. 20157909.1.

Notice of Allowance dated Aug. 4, 2020 issued for corresponding U.S. Appl. No. 16/277,186.

EP Search Report dated Aug. 3, 2020, issued for corresponding European Patent Application No. 20157772.3.

U.S. Non-Final Office action dated Feb. 11, 2021 issued for corresponding U.S. Appl. No. 16/278,411.

\* cited by examiner

ACTIVE OIL DEBRIS MONITOR PHASE ANGLE CALCULATION AND MONITORING SYSTEM

BACKGROUND

The present disclosure relates to an oil system for a gas turbine engine and, more particularly, to an on-board system for actively calculating and monitoring an oil debris monitor phase angle.

Many types of mechanical machinery include various components that require lubrication. For example, gas turbine engines typically have gears and bearings that require a lubricating liquid, such as oil, to lubricate and cool those gears and bearings during operation. During operation, debris accumulates in the lubricating liquid. Because of this, lubrication systems typically include an oil debris monitor system to sense metal debris in the oil. An oil debris monitor system is normally used to flag the initiation or progression of mechanical failures in the lubricated mechanical machinery.

It is extremely difficult to validate the accuracy of an oil debris monitor system while it is installed in a lubrication system. Thus, it is important to validate the accuracy of an oil debris monitor prior to it being installed in the lubrication system. It can also be difficult to reliably validate accuracy of an oil debris monitor in a lab with known validation methods, especially in a lab that does not allow oil to be present. An oil debris monitor phase angle is often used to classify detected particle types (ferrous/nonferrous) through a mathematical transformation. Currently, the phase angle is hardcoded into the system. The phase angle is determined by an offline calibration test process and the resultant value calculated. In legacy systems, the phase angle applied to oil debris monitor data for particle detection is a fixed value in the software. However, the proper phase angle for an individual oil debris monitor is a function of system capacitance and inductance, so every oil debris monitor sensor phase angle is different and can change based on system condition and related system components. The use of an improper phase angle can reduce the system capability to detect particles and can also lead to particle type and size misclassification. Furthermore, a system phase angle should be fixed, and any sudden changes or instability in phase angle may be indicative of system deterioration.

SUMMARY

A method for actively calculating and monitoring oil debris monitor phase angle in an oil system, according to one disclosed non-limiting embodiment of the present disclosure includes sensing a noise from an in-line oil debris monitor sensor in an oil flow path of the oil system; generating a polar plot of an I and Q channel data from only the noise; identifying a multiple of noise peaks in the polar plot; determining a linear regression of the noise peaks; calculating a slope of regression from the linear regression; and converting the slope to a phase angle.

A further aspect of the present disclosure includes that identifying the noise peak determines the outer bounds of the polar plot.

A further aspect of the present disclosure includes that the oil flow path is an oil supply path.

A further aspect of the present disclosure includes that the oil flow path is an oil return path.

A further aspect of the present disclosure includes, storing the calculated phase angle.

A further aspect of the present disclosure includes utilizing the calculated phase angle for health and stability assessment.

A further aspect of the present disclosure includes, transmitting the calculated phase angle for health and stability assessment.

A further aspect of the present disclosure includes, converting raw oil debris monitor data from the in-line oil debris monitor sensor from analog to digital.

A further aspect of the present disclosure includes, converting the raw oil debris monitor data from in-line oil debris monitor sensor within a controller on-board an aircraft.

A further aspect of the present disclosure includes, continually filling a buffer of the controller with the raw oil debris monitor data.

A further aspect of the present disclosure includes that the phase angle is calculated in essentially real time.

A further aspect of the present disclosure includes, using the phase angle to classify detected particle types.

A further aspect of the present disclosure includes that the particle types comprise ferrous or nonferrous particle types.

An oil system for a gas turbine engine according to one disclosed non-limiting embodiment of the present disclosure includes an oil flow path; an in-line oil debris monitor sensor; and a control system in communication with the in-line oil debris monitor sensor to determine a phase angle of I and Q channel data from only the noise from the in-line oil debris monitor sensor.

A further aspect of the present disclosure includes that the oil flow path is in communication with a geared architecture of the gas turbine engine.

A further aspect of the present disclosure includes that the oil flow path is an oil supply path.

A further aspect of the present disclosure includes that the oil flow path is an oil return path.

A further aspect of the present disclosure includes, a chip collector within the oil flow path.

A further aspect of the present disclosure includes that the control system comprises a controller on-board an aircraft.

The foregoing features and elements may be combined in various combinations without exclusivity, unless expressly indicated otherwise. These features and elements as well as the operation thereof will become more apparent in light of the following description and the accompanying drawings. It should be appreciated; however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
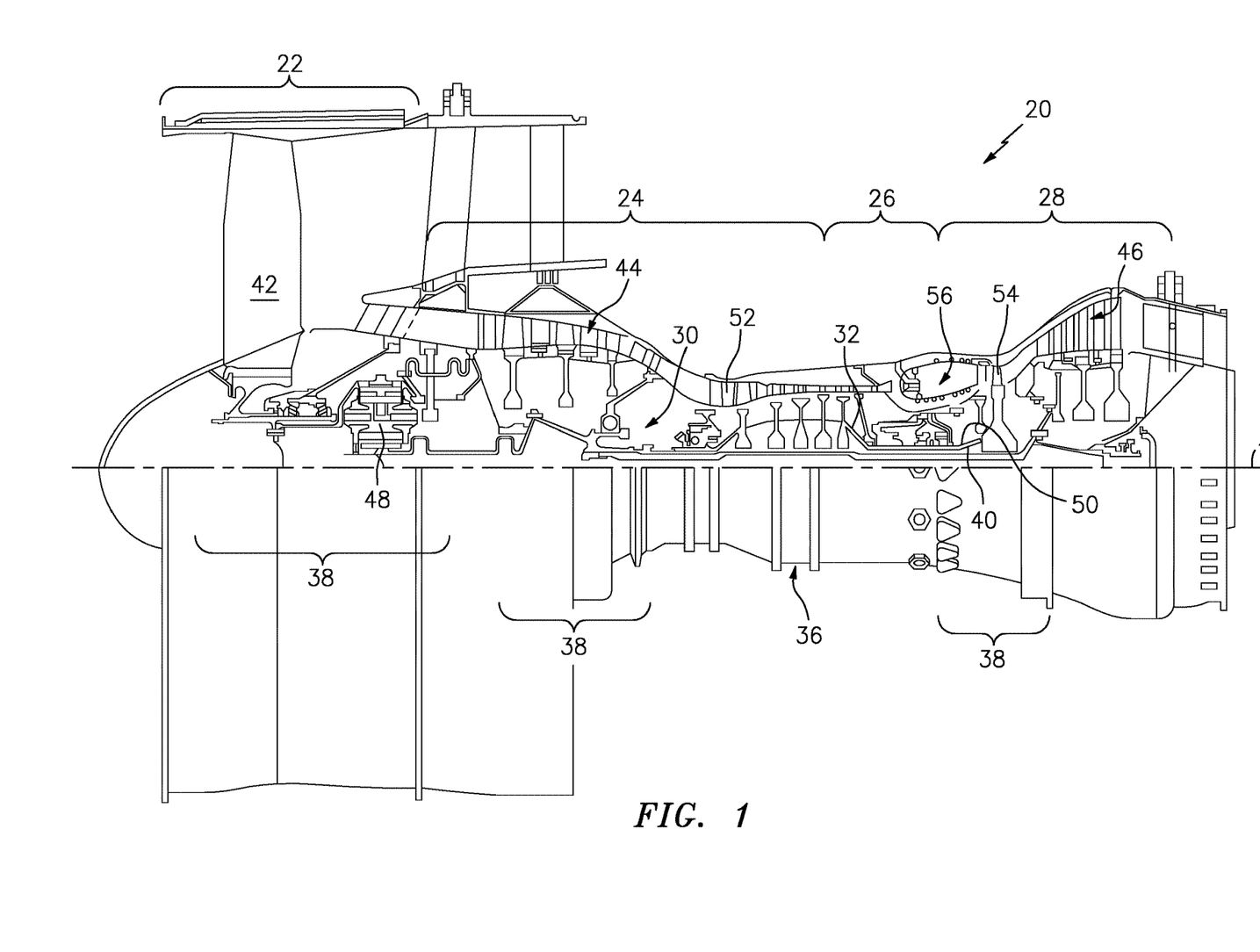
FIG. 1 is a schematic cross-section of an example gas turbine engine architecture.

FIG. 1 schematically illustrates a gas turbine engine 20. The gas turbine engine 20 is disclosed herein as a two-spool turbofan that generally incorporates a fan section 22, a compressor section 24, a combustor section 26, and a turbine section 28. The fan section 22 drives air along a bypass flowpath while the compressor section 24 drives air along a core flowpath for compression and communication into the combustor section 26, then expansion through the turbine section 28. Although depicted as a turbofan in the disclosed non-limiting embodiment, it should be appreciated that the concepts described herein may be applied to other engine architectures such as turbojets, turboshafts, and three-spool (plus fan) turbofans.

The engine 20 generally includes a low spool 30 and a high spool 32 mounted for rotation about an engine central longitudinal axis X relative to an engine static structure 36 via several bearings 38. The low spool 30 generally includes an inner shaft 40 that interconnects a fan 42, a low pressure compressor ("LPC") 44 and a low pressure turbine ("LPT") 46. The inner shaft 40 drives the fan 42 directly or through a geared architecture 48 that drives the fan 42 at a lower speed than the low spool 30. An exemplary reduction transmission is an epicyclic transmission, such as a planetary or star gear system.

The high spool 32 includes an outer shaft 50 that interconnects a high pressure compressor ("HPC") 52 and high pressure turbine ("HPT") 54. A combustor 56 is arranged between the high pressure compressor 52 and the high pressure turbine 54. The inner shaft 40 and the outer shaft 50 are concentric and rotate about the engine central longitudinal axis X which is collinear with their longitudinal axes.

Core airflow is compressed by the LPC 44, then the HPC 52, mixed with the fuel and burned in the combustor 56, then expanded over the HPT 54 and the LPT 46 which rotationally drive the respective high spool 32 and the low spool 30 in response to the expansion. The main engine shafts 40, 50 are supported at a plurality of points by bearings 38 within the static structure 36.

Figure 2:
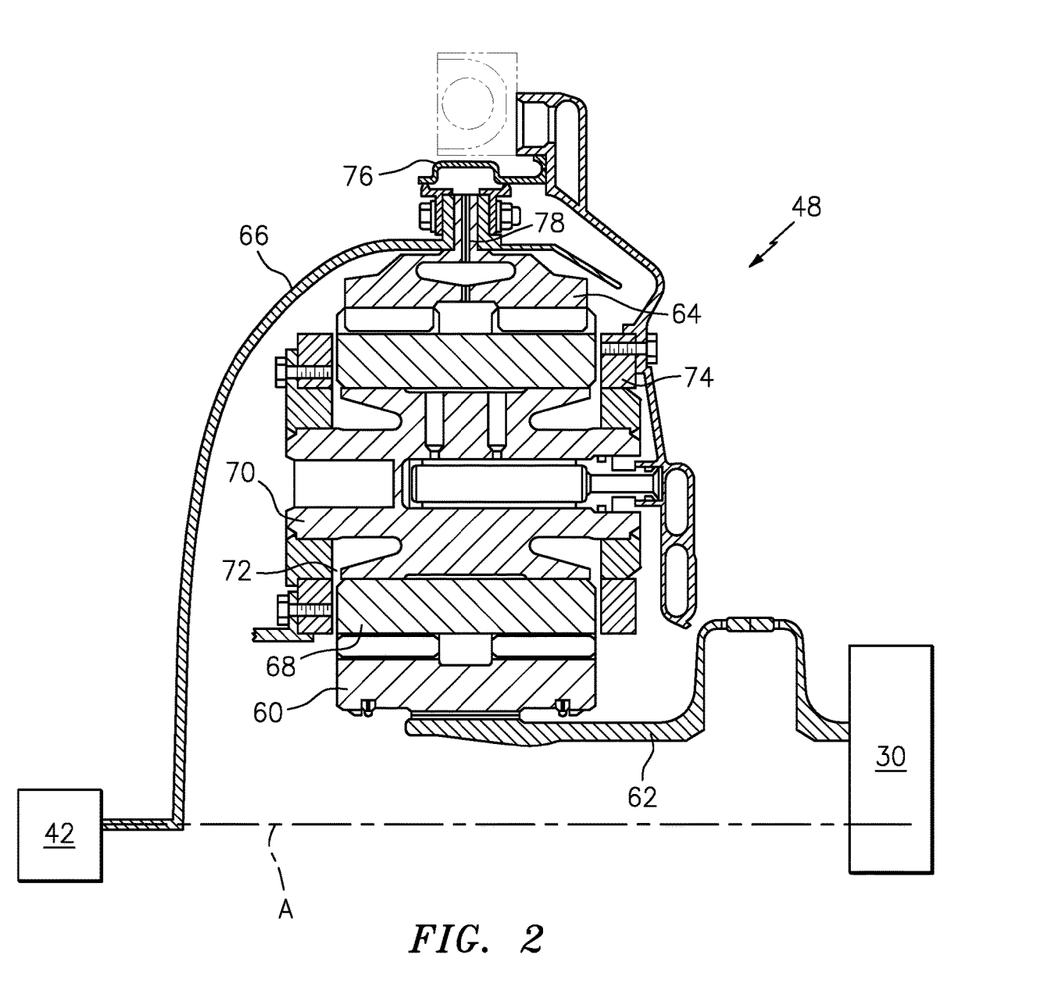
FIG. 2 is a schematic cross-section of a geared architecture for a gas turbine engine.

With reference to FIG. 2, the geared architecture 48 includes a sun gear 60 driven by a sun gear input shaft 62 from the low speed spool 30, a ring gear 64 connected to a ring gear output shaft 66 to drive the fan 42 and a set of intermediate gears 68 in meshing engagement with the sun gear 60 and ring gear 64. Each intermediate gear 68 is mounted about a journal pin 70 which are each respectively supported by a carrier 74. The input shaft 62 and the output shaft 66 counter-rotate as the sun gear 60 and the ring gear 64 are rotatable about the engine central longitudinal axis A. The carrier 74 is grounded and non-rotatable even though the individual intermediate gears 68 are each rotatable about their respective axes 80. An oil recovery gutter 76 is located around the ring gear 64. The oil recovery gutter 76 may be radially arranged with respect to the engine central longitudinal axis A.

A replenishable film of oil, not shown, is supplied to an annular space 72 between each intermediate gear 68 and the respective journal pin 70. One example applicable oil meets U.S. Military Specification MIL-PRF-23699, for example, Mobil Jet Oil II manufactured by ExxonMobil Aviation, United States. Oil is supplied through the carrier 74 and into each journal pin 70 to lubricate and cool the gears 60, 64, 68 of the geared architecture 48. Once communicated through the geared architecture 48 the oil is radially expelled through the oil recovery gutter 76 in the ring gear 64 by various paths such as oil passage 78.

Figure 3:
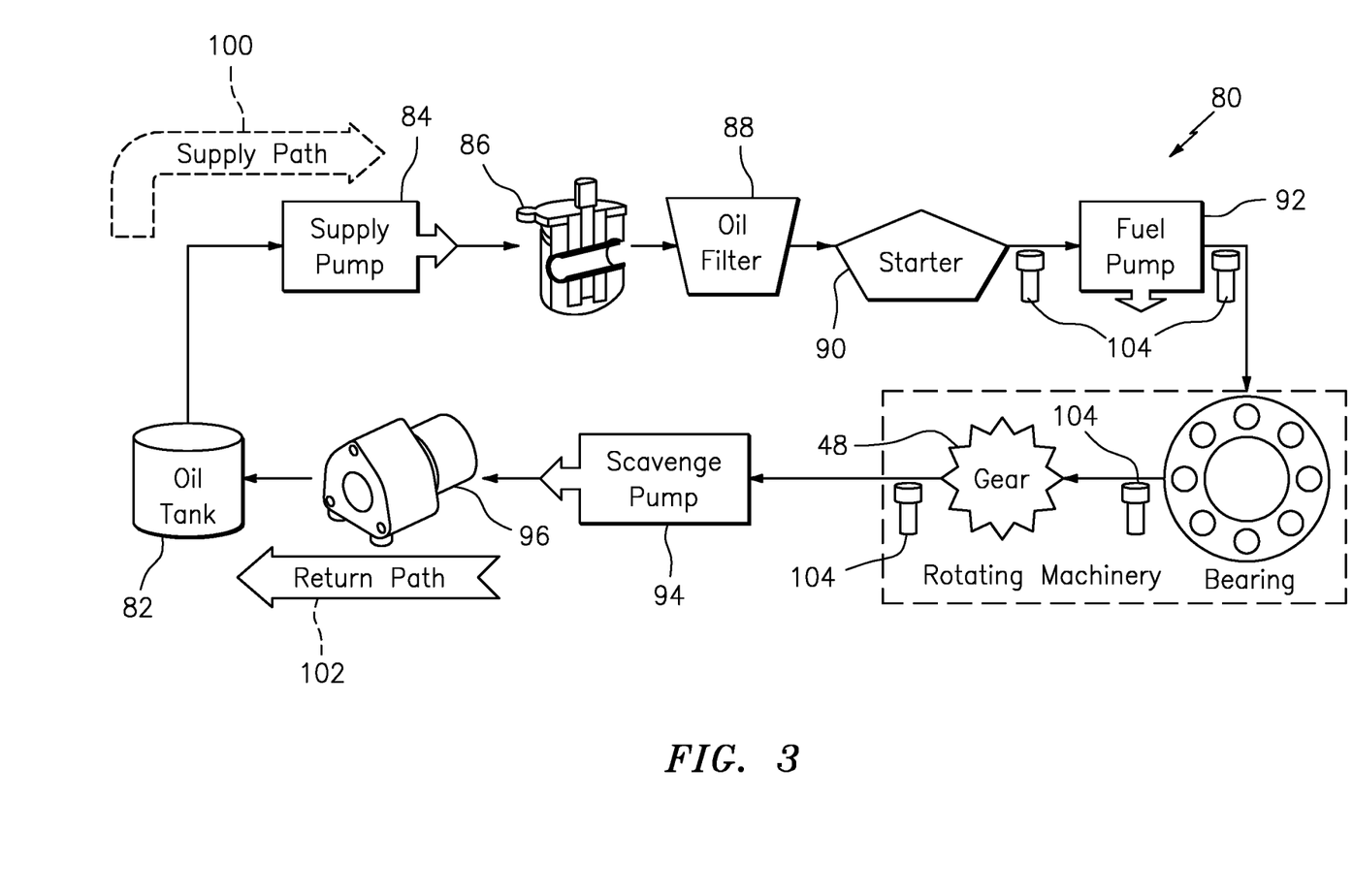
FIG. 3 is a schematic diagram of an oil system for a geared architecture gas turbine engine.

With reference to FIG. 3, an oil system 80 is schematically illustrated in block diagram form for the geared architecture 48 as well as other components which receive oil. It should be appreciated that the oil system 80 is but a schematic illustration and is simplified in comparison to an actual oil system. The oil system 80 generally includes an oil tank 82, a supply pump 84, a sensor 86, an oil filter 88, a starter 90, a fuel pump 92, the geared architecture 48, the scavenge pump 94, and a sensor 96. The oil flow to the geared architecture 48 may be considered an oil supply path 100, and the oil flow from the geared architecture 48 can be considered an oil return path 102. A multiple of chip collectors 104 may be located in the supply path 100 and the return path 102 to capture ferrous debris.

The sensors 86, 96 may utilize two outer field coils to generate a drive signal (high frequency cyclic signal), causing equal and opposing magnetic fields (M-field). The ferrous particle strength of the M-field created by one field coil after another, causes the processed signal to be a period of a sine wave. The non-ferrous particle weakens the M-field created by one field coil after another, causing the similar sine wave but in opposing polarity. Generally, the signal magnitude is proportional to the size of particle and the signal width is inversely proportional to the particle speed.

Figure 4:
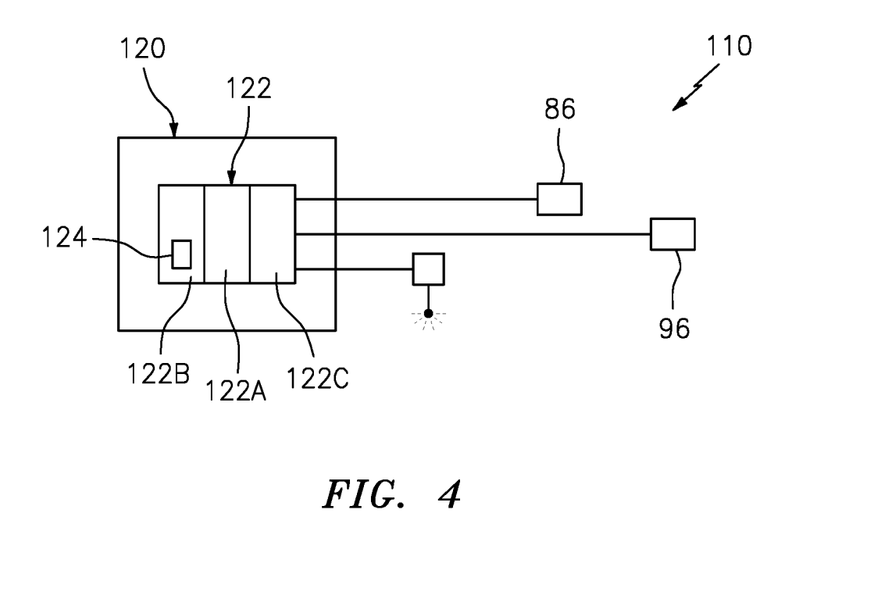
FIG. 4 is a schematic diagram of a debris management system according to one disclosed non-limiting embodiment.

With Reference to FIG. 4, a debris management system 110 generally includes a controller 120 in communication with the sensors 86, 96. The sensors 86, 96 may be in-line oil debris monitor sensors. The debris management system 110 protects against unexpected phase angle changes which may affect individual oil debris monitors caused by replacement or redesign of other components in the system, such as a signal wire harness, that can drastically influence the phase angle.

The controller 120 generally includes a control module 122 that executes logic 124 (FIG. 5) to actively calculate and monitor the oil debris monitor phase angle with regards to particle detection and system deterioration, stability and health. The functions of the logic 124 are disclosed in terms of functional block diagrams, and it should be appreciated that these functions may be enacted in either dedicated hardware circuitry or programmed software routines capable of execution in a microprocessor-based electronics control embodiment. In one example, the control module 122 may be a portion of a flight control computer, a portion of a Full Authority Digital Engine Control (FADEC), a stand-alone unit, or other system.

The control module 122 includes a processor 122A, a memory 122B, and an interface 122C. The processor 122A may be any type of known microprocessor having desired performance characteristics. The memory 122B may be any computer readable medium which stores data and control algorithms such as the logic 124 as described herein. The interface 122C facilitates communication with other components such as the sensors 86, 96, as well as remote systems such as a ground station, Health and Usage Monitoring Systems (HUMS), or other system.

The oil debris monitor phase angle is used to classify detected particle types (Ferrous/nonferrous) through a mathematical transformation. The phase angle is calibrated by pulling a particle of known type and size through the sensor and using the ratio of I and Q channel amplitude and trigonometric relationships to calculate an optimum (for classification) phase angle. The I channel is the In-phase, or real component and the Q channel is the Quadrature (90° shift of real component). As will be further described below, this principle is applied to background noise in the system by calculating the slope of the relationship between noise peaks of the oil debris monitor I and Q data channels.

Figure 5:
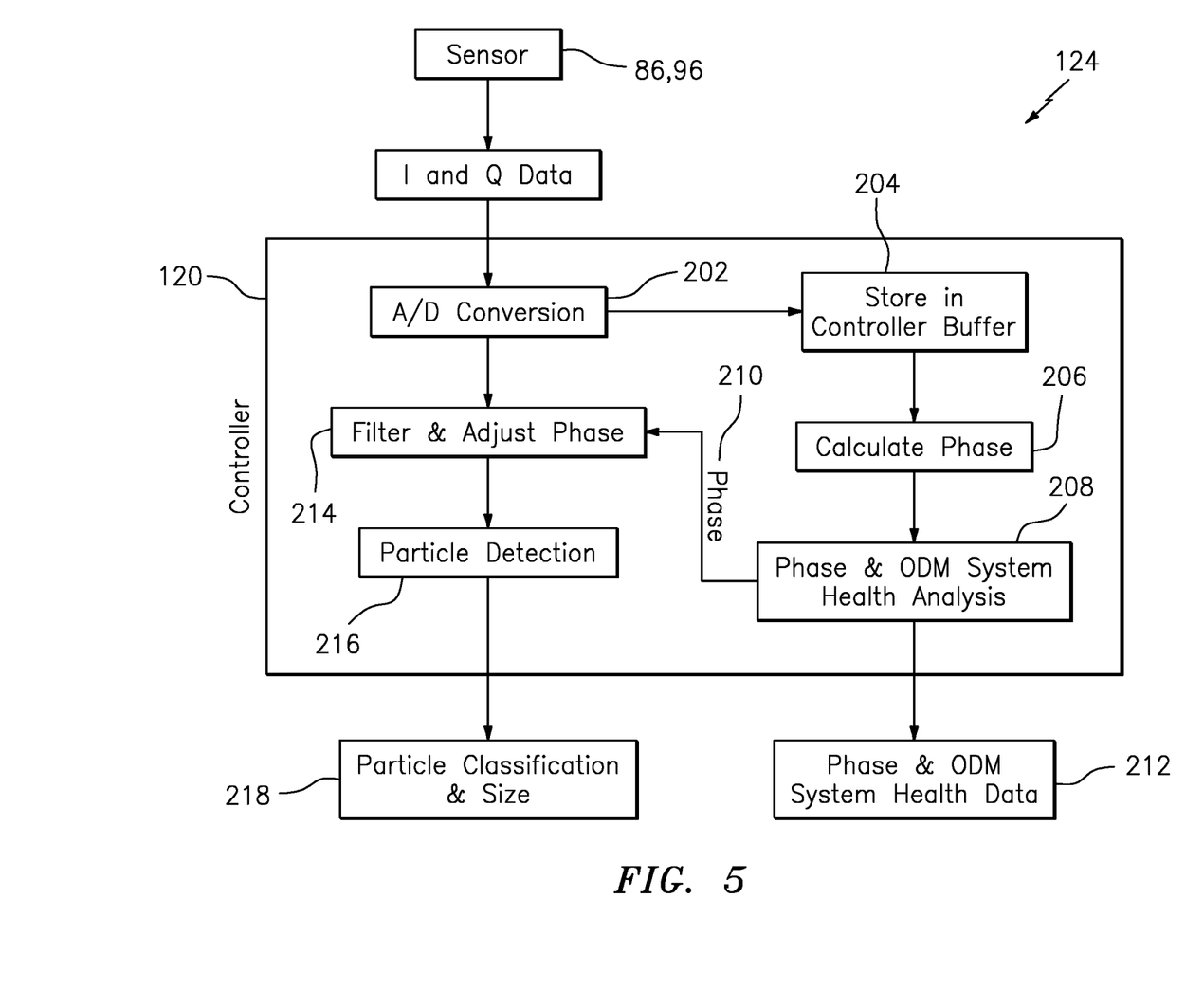
FIG. 5 is a block diagram representative of logic for the debris management system.

With reference to FIG. 5, the logic 124 for particle analysis initially includes receipt of raw oil debris monitor data from either or both of the sensors 86, 96 into the controller 120 for signal conversion from analog to digital (202). The raw data is stored in the controller buffer (204). The buffer for the controller 120 is continually filled with raw data that flows as a constant stream such that a running on-board calculation may be performed.

Figure 6:
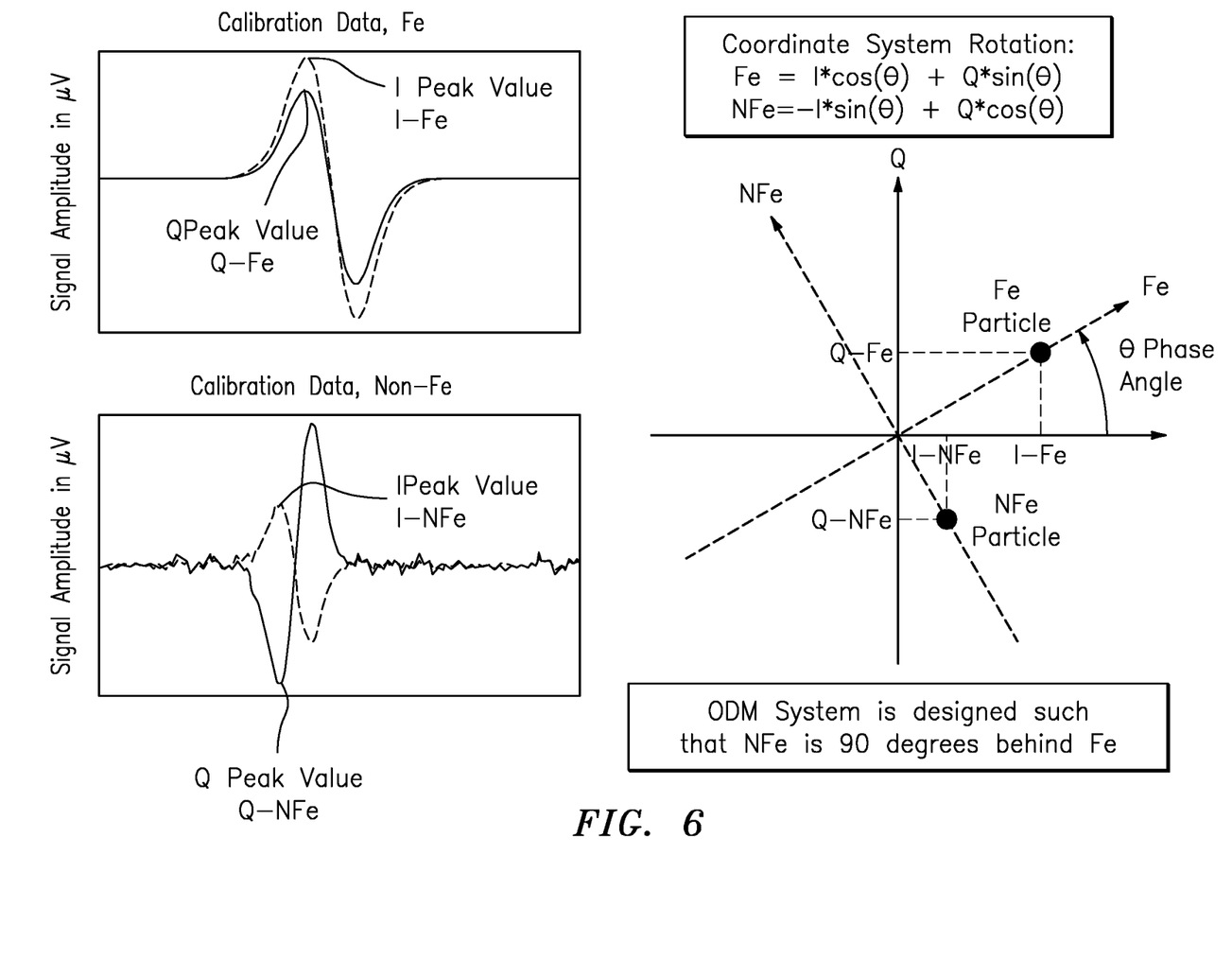
FIG. 6 is a schematic representation of a coordinate system to determine phase angle.
Figure 7:
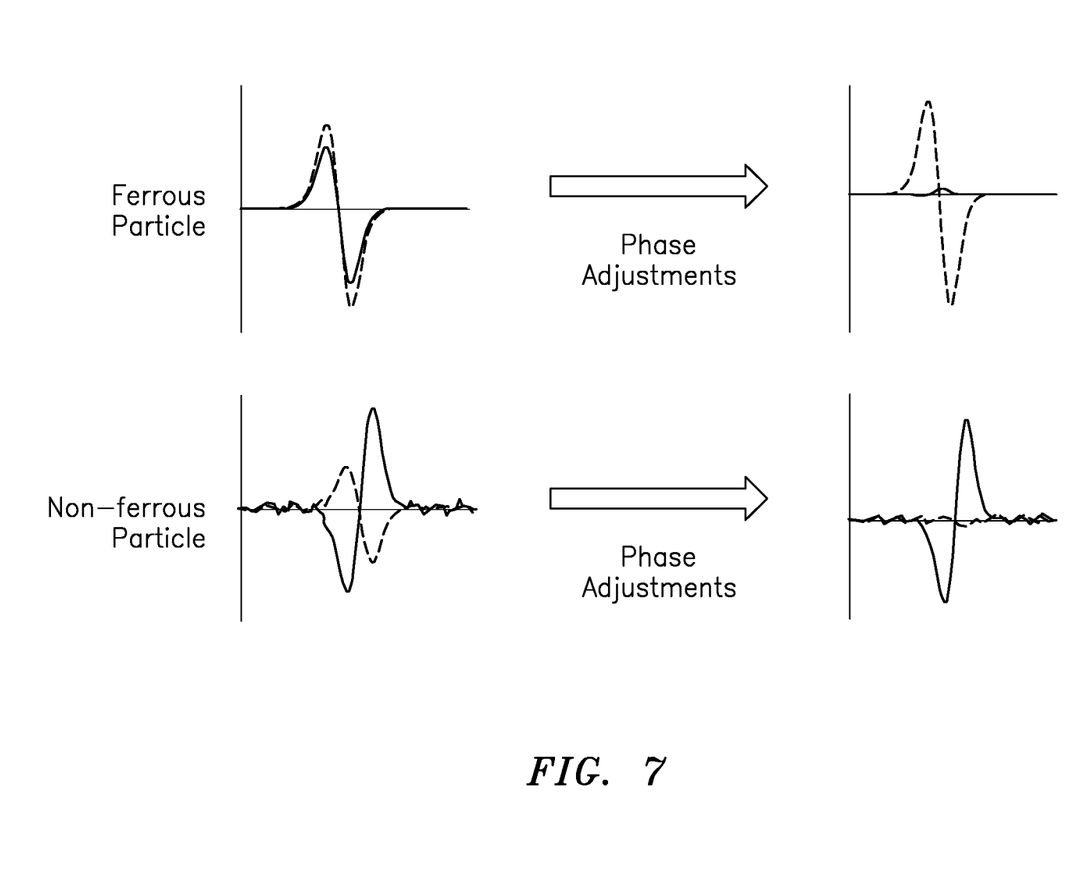
FIG. 7 is a graphical representation of a phase adjustment of the phase angle for a ferrous and non-ferrous particle by the on-board controller.
Figure 8:
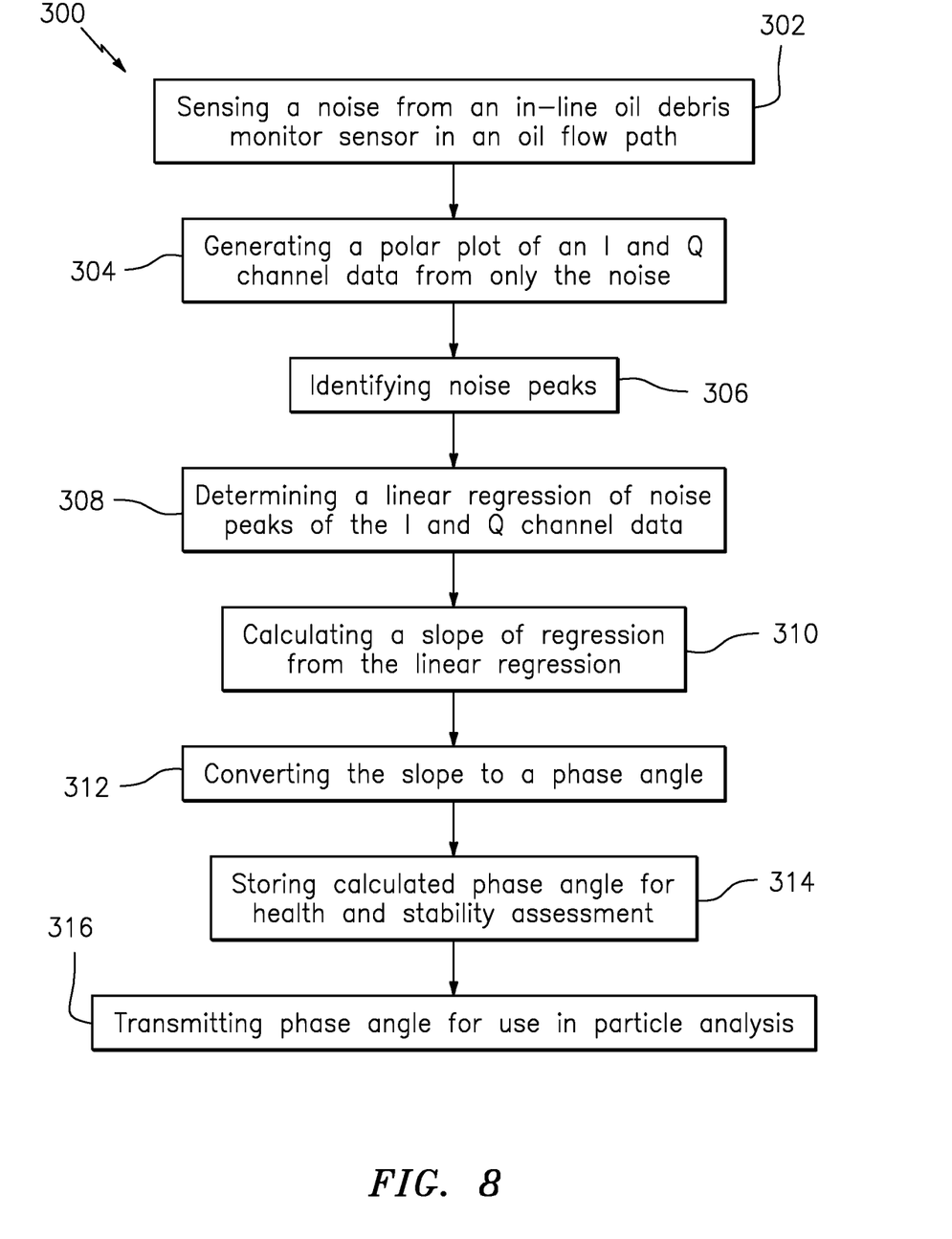
FIG. 8 is a block diagram representative of a method that determines on-board controller controller as shown in calculate phase of FIG. 5.
Figure 9:
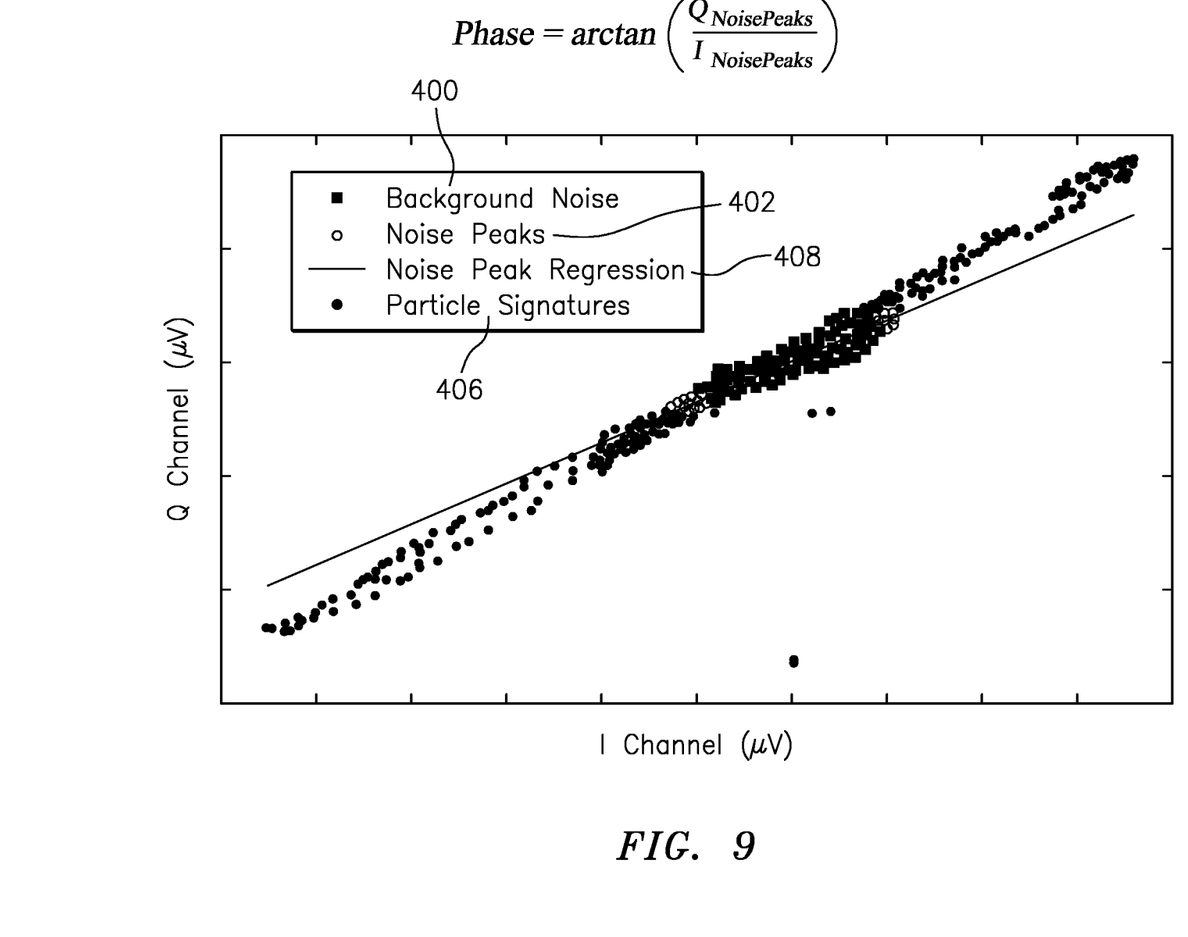
FIG. 9 is a graphical representation of a phase angle determination.

The phase angle of the signal (206; FIG. 6) is calculated from the noise using the raw oil debris monitor data in the controller buffer. The phase angle may then be used for a system health assessment (208) and may be transmitted (210) for further processing in the controller as well as transmitted with system health data for off board health monitoring (212). The system health assessment may include, for example, particle count, particle type classification, size and mass estimates, system availability, debris count rates, and other metrics. The A/D converted raw oil debris monitor signals are filtered and phase angle adjusted (214) within the controller, then the particle detection algorithm executes (216). Typically, the particle signal will distribute into both I and Q channels due to phase angle misalignment between the drive signal and mixer signal as caused by system impedance in the driving and sensing circuitry. The phase angle adjustment (FIG. 7) realigns the particle signal distribution such that the ferrous particle signal is maximized in the ferrous channel and the non-ferrous particle signal is maximized in then non-ferrous channel. The particle classification and size data from the particle detection algorithm is then transmitted (218) for off board health monitoring. With reference to FIG. 9, a method 300 for actively calculating and monitoring the oil debris monitor phase angle on board the controller initially includes accessing the oil debris monitor raw data from the controller buffer which has been obtained from the sensors 86, 96 (204; FIG. 5). Next, a polar plot of the I and Q data is created from the background noise 400 only (step 304; FIG. 9). Essentially, the noise 400 (FIG. 10) is isolated as compared to the particle signal 406 (FIG. 8) from actual particles.

Next, noise peaks (402; (FIG. 9)) which are the outer bounds of the polar plot are identified (step 306). Noise peaks are the outer bounds of the polar plot that may not be attributed to a particle.

Figure 10:
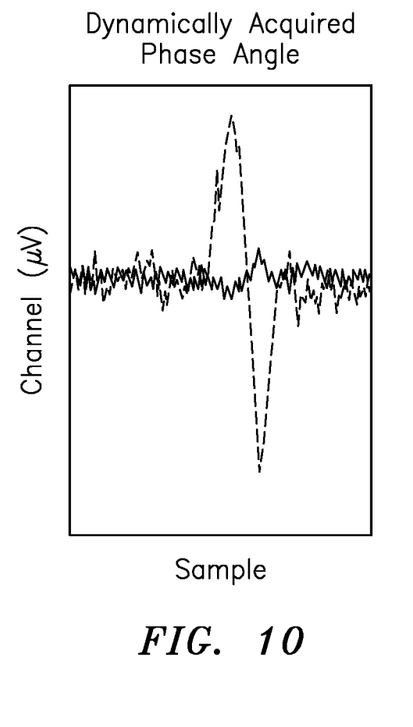
FIG. 10 is a graphical representation of a dynamically adjusted phase angle determination.
Figure 11:
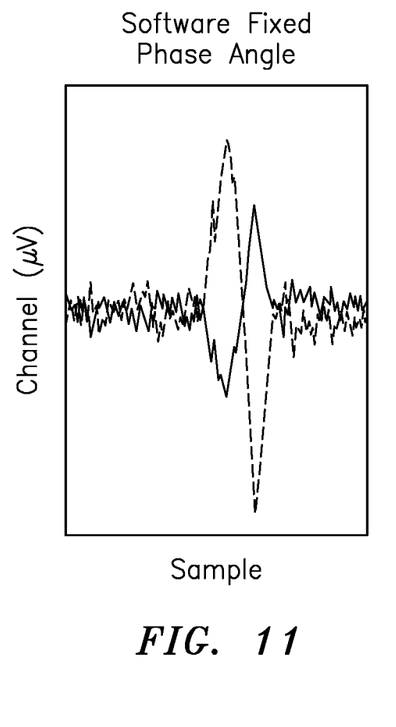
FIG. 11 is a graphical representation of a software fixed phase angle determination.
Figure 12:
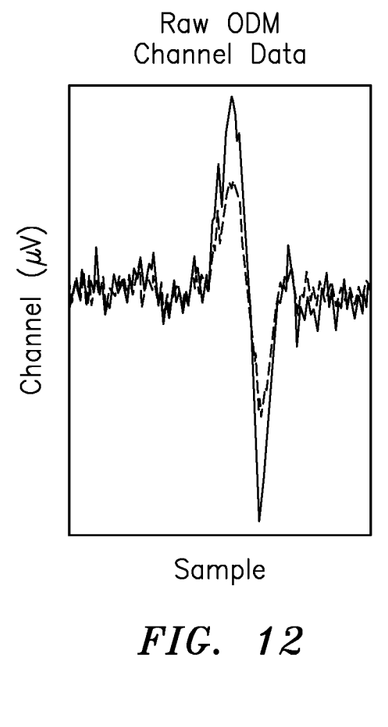
FIG. 12 is a graphical representation of raw ODM channel data.

A linear noise peak regression (408; (FIG. 9)) of the I and Q data noise peaks is then performed (step 308). The linear noise peak regression generates a line with a slope that is used to calculate phase. For example, linear regression may be utilized generally or specifically with the peaks. Next, a slope of linear noise peak regression is calculated (step 310) then converted to phase angle (step 312). The slope may be determined with the arc tan formula (FIG. 10). In current systems, the phase angle is a fixed value in the software based on calibration tests and peaks of the particles are utilized to calculate the phase angle. In contrast, by focusing on the noise, the phase angle is calculated in essentially real time. For example, the phase angle may be calculated to be about 125% (FIG. 10) compared to a software fixed value (FIG. 11) based on the same raw ODM channel data (FIG. 12). The noise provides a calculated phase angle to show the ferrous particle without any non-ferrous excitation. For example, the planner plot shows the fixed phase angle of the system (FIG. 10) compared to use of noise feedback (FIG. 11).

Figure 13:
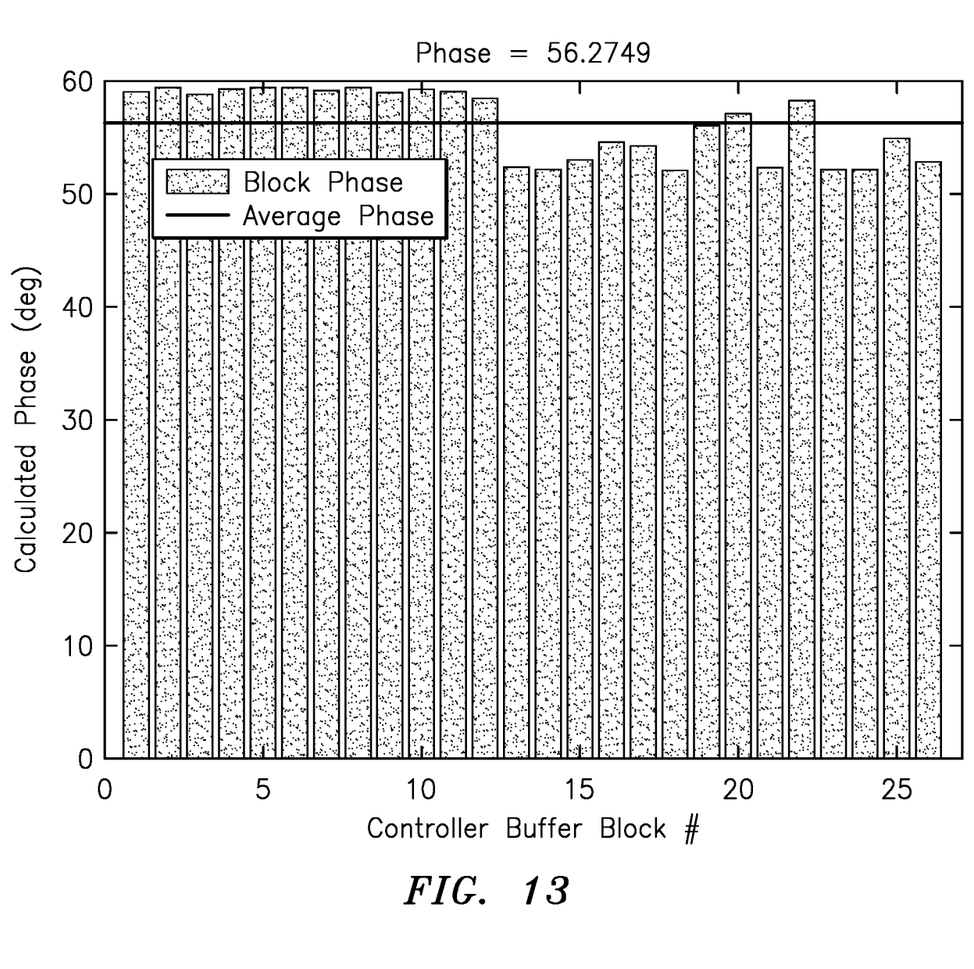
FIG. 13 is a graphical representation of a dynamically adjusted phase angle determination in a stable condition as determined within the on-board controller.

The calculated phase angle may then be stored (step 314) and/or transmitted (step 316) for heath and stability assessment. The system is thus identified as healthy when the phase angle is stable (FIG. 13) compared to an unhealthy system that is not stable to provide another point for off-board trending.

The method 300 dynamically identifies the effect of phase angle change and adopts the appropriate phase angle. The real time phase angle can be determined onboard and used to provide a more accurate particle size and classification to determine the health of the diagnostic system and also provide a tool for predicting the state of the system in the future.

Although particular step sequences are shown, described, and claimed, it should be appreciated that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason, the appended claims should be studied to determine true scope and content.

What is claimed:

1. A method for actively calculating and monitoring oil debris monitor phase angle in an oil system, comprising:
sensing a noise from an in-line oil debris monitor sensor in a flow of oil in an oil flow path of the oil system;
generating a polar plot of an I and Q channel data from only the noise;
identifying a multiple of noise peaks in the polar plot;
determining a linear regression of the noise peaks;
calculating a slope of regression from the linear regression;
converting the slope to a calculated phase angle; and
comparing the calculated phase angle to a known phase angle for the oil debris monitor sensor to determine if the calculated phase angle is stable and therefore that the oil system is functioning properly, or the calculated phase angle is unstable and the oil system needs maintenance.

2. The method as recited in claim 1, wherein identifying the noise peak determines the outer bounds of the polar plot.

3. The method as recited in claim 1, wherein the oil flow path is an oil supply path.

4. The method as recited in claim 1, wherein the oil flow path is an oil return path.

5. The method as recited in claim 1, further comprising storing the calculated phase angle.

6. The method as recited in claim 5, further comprising utilizing the calculated phase angle for health and stability assessment.

7. The method as recited in claim 1, further comprising transmitting the calculated phase angle for health and stability assessment.

8. The method as recited in claim 1, further comprising converting raw oil debris monitor data from the in-line oil debris monitor sensor from analog to digital.

9. The method as recited in claim 8, further comprising converting the raw oil debris monitor data from in-line oil debris monitor sensor within a controller on-board an aircraft.

10. The method as recited in claim 9, further comprising continually filling a buffer of the controller with the raw oil debris monitor data.

11. The method as recited in claim 1, wherein the phase angle is calculated in essentially real time.

12. The method as recited in claim 1, further comprising using the phase angle to classify detected particle types.

13. The method as recited in claim 12, wherein the particle types comprise ferrous or nonferrous particle types.

14. An oil system for a gas turbine engine, comprising:
an oil flow path;
an in-line oil debris monitor sensor for sensing a noise in a flow of oil along the oil flow path; and
a control system in communication with the in-line oil debris monitor sensor and configured to calculate a slope of a linear regression from the noise; convert the slope to a calculated phase angle; and compare the calculated phase angle to a known phase angle of the oil debris monitor sensor to determine if the calculated phase angle is stable and therefore that the oil system is functioning properly, or the calculated phase angle is unstable and the oil system needs maintenance.

15. The system as recited in claim 14, wherein the oil flow path is in communication with a geared architecture of the gas turbine engine.

16. The system as recited in claim 14, wherein the oil flow path is an oil supply path.

17. The system as recited in claim 14, wherein the oil flow path is an oil return path.

18. The system as recited in claim 14, further comprising a chip collector within the oil flow path.

19. The system as recited in claim 14, wherein the control system comprises a controller on-board an aircraft.

* * * * *